United States Patent [19]

Hrib et al.

[11] Patent Number: 5,272,148
[45] Date of Patent: Dec. 21, 1993

[54] HETEROARENYLPIPERAZINES

[75] Inventors: Nicholas J. Hrib, Somerville; John G. Jurcak, Union City, both of N.J.

[73] Assignee: Hoechst-Roussel Pharmaceuticals Incorporated, Somerville, N.J.

[21] Appl. No.: 942,232

[22] Filed: Sep. 9, 1992

[51] Int. Cl.$^5$ .................. A61K 31/495; C07D 401/04
[52] U.S. Cl. .................... 514/254; 544/230; 544/362; 514/253
[58] Field of Search ............... 544/362, 230; 514/253, 514/254

[56] References Cited

U.S. PATENT DOCUMENTS

| | | | |
|---|---|---|---|
| 3,654,204 | 4/1972 | Klum et al. | 544/278 |
| 4,677,104 | 6/1987 | New et al. | 544/230 |
| 4,710,500 | 12/1987 | Perregaard | 514/254 |
| 5,143,923 | 9/1992 | Hrib et al. | 514/321 |
| 5,240,927 | 8/1993 | Hrib et al. | 514/254 |

OTHER PUBLICATIONS

A. D. Dunn et al., Journal of Heterocyclic Chemistry, vol. 24, pp. 85-89, Publ. Jan.-Feb. 1986, "Nucleophilic Displacements in Pyridine Rings".
S. W. Schneller et al., Journal of Heterocyclic Chemistry, vol. 13, pp. 273-275, Pub. Apr. 1, 1976, entitled: "A Simple Synthesis of Thieno[2,3-b]pyrazine and Thieno[2,3-b]pyridine".

*Primary Examiner*—Cecilia Tsang
*Attorney, Agent, or Firm*—Raymond R. Wittekind

[57] ABSTRACT

Novel heteroarenylpiperazines, intermediates and processes for the preparation thereof, and methods for treating psychoses utilizing compounds or compositions thereof are disclosed.

15 Claims, No Drawings

HETEROARENYLPIPERAZINES

The present invention relates to heteroarenylpiperazines. More particularly, the present invention relates to heteroarenylpiperazines of formula 1

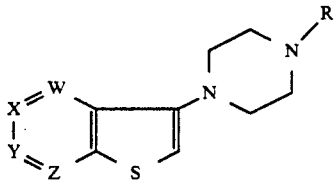

wherein:
(a) W, X, Y, and Z are independently CH or nitrogen, with the proviso that at one or two of W, X, Y, or Z are nitrogen;
(b) R is hydrogen, loweralkyl, a group of the formula

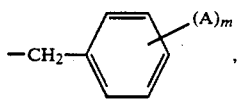

a group of the formula

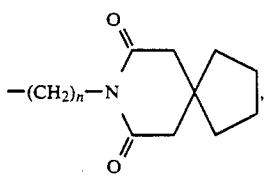

a group of the formula

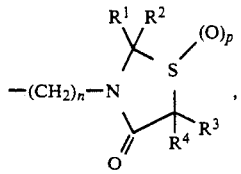

or a group of the formula

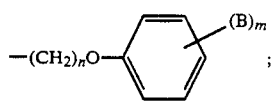

(c) $R^1$, $R^2$, $R^3$, and $R^4$ are independently hydrogen or loweralkyl, or $R^1$ and $R^2$ or $R^3$ and $R^4$ taken together with the carbon atom to which they are attached form a cycloalkyl ring;
(d) A is hydrogen, loweralkyl, loweralkoxy, halogen, or trifluoromethyl;
(e) B is hydrogen, loweralkyl, loweralkoxy, hydroxy, amino, aminoloweralkyl, halogen, trifluoromethyl, a group of the formula

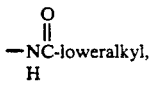

or a group of the formula

wherein $R^5$ is loweralkyl, loweralkoxy, amino, loweralkylamino, or diloweralkylamino;
(f) m is 1 or 2;
(g) n is 2 to 4;
(h) p is 0, 1, or 2,
the optical antipodes thereof, or the pharmaceutically acceptable acid addition salts thereof, which are useful for treating psychoses, alone or in combination with adjuvants, and as intermediates for the preparation thereof.

Subgeneric to the heteroarenylpiperazines of the present invention are compounds of formula 1 wherein:
(a) W, X, and Y are CH and Z is nitrogen; and
(b) W, X, and Z are CH and Y is nitrogen.

Preferred heteroarenylpiperazines of the present invention are compounds of formula 1 wherein:
(a) W, X, Y, and Z are as immediately above; and
(b) R is hydrogen; a group of the formula

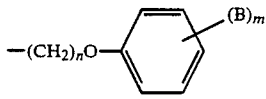

wherein B is loweralkoxy or a group of the formula

wherein $R^5$ is loweralkyl; or a group of the formula

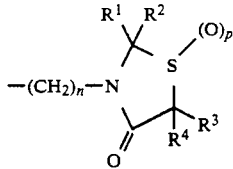

wherein $R^1$ is hydrogen, $R^2$, $R^3$, and $R^4$ are loweralkyl, and p is 0.

As used through the specification and appended claims, the term "alkyl" refers to a straight or branched chain hydrocarbon radical containing no unsaturation and having 1 to 10 carbon atoms such as methyl, ethyl, n-propyl, i-propyl, n-butyl, n-pentyl, isopentyl, heptyl, octyl, decyl and the like; the term "cycloalkyl" refers to a saturated hydrocarbon group possessing at least one carbocyclic ring, the ring containing from 3 to 7 carbon atoms such as cyclopropyl, cyclobutyl, cyclopentyl, cychexyl, cycoheptyl and the like; the term "alkoxy" refers to a monovalent substituent which consists of an alkyl group linked through an ether oxygen and having its free valence bond from the ether oxygen such as methoxy, ethoxy, isopropoxy, n-butoxy, tert-butoxy, n-pentoxy, isopentoxy, heptoxy, hexoxy, octoxy, decoxy and the like; the term "halogen" refers to a member of the family fluorine, chlorine, bromine or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel heteroarenylpiperazines of the present invention and the intermediates thereto are prepared by the reaction sequence illustrated in the Reaction Scheme. A 3-aminothiophene-2-carboxylic acid alkyl ester 2, the preparation of which is described in A. D. Dunn and R. Norrie, Journal of Heterocyclic Chemistry, 24, 85 (1987), is decarboxyalkylated to a 3-aminothiophene 3, which is condensed with piperazine 5

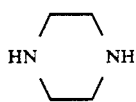

5 to afford an intermediate thien-3-ylpiperazine 4, and, in turn, alkylated with a halide 6

RHal                    6 wherein R is as hereinbeforedescribed and Hal is bromo or chloro to provide an ultimate, N-substituted thien-3-ylpiperizine 1 wherein W, X, Y, Z, and R are also as hereinbeforedescribed.

The decarboxyalkylation is performed by heating a 3-aminothiophene-2-carboxylic acid alkyl ester 2 at an elevated temperature of about 125° to about 175° C. in a dipolar aprotic solvent in the presence of piperazine to provide amine 3. Among dipolar aprotic solvents, there may be mentioned dimethylformamide, dimethylacetamide, and N-methylpyrrolidinone, N-methylpyrrolidinone being preferred. Also preferred is a reaction temperature of about 150° C.

The condensation of a 3-aminothiophene 3 with piperazine 5 is conveniently carried out in an dipolar aprotic solvent such as those mentioned above, namely, dimethylformamide, dimethylacetamide, and N-methylpyrrolidinone, N-methylpyrrolidinone being preferred, in the presence of an organic acid at the reflux temperature of the condensation medium. Included among organic acids are benzenesulfonic acid and p-toluenesulfonic acid. p-Toluenesulfonic acid being preferred.

The transformation of a 3-aminothiophene-2-carboxylic acid alkyl ester 2 to a thien-3-ylpiperazine 4 may be effected, without isolation of the 3-aminothiophene 3, by adding the organic acid to the initial reaction mixture after the decarboxyalkylation is complete.

The alkylation of thien-3-ylpiperazine 4 with halide 6 is accomplished by treating piperazine 4 with halide 6, in an organic solvent in the presence of an acid acceptor. Organic solvents include acetonitrile and the aforementioned polar aprotic solvents, (e.g., dimethylacetamide and dimethylformamide), acetonitrile being the preferred organic solvent. Acid acceptors include alkali metal carbonates and bicarbonates such as sodium or potassium carbonate and sodium or potassium bicarbonate. Potassium carbonate is preferred. While the alkylation temperature is not narrowly critical, it is preferred to carry out the reaction at a temperature of about 50°-100° C., a reaction temperature within the range of about 75° to 85° C. being most preferred.

To promote the alkylation, it is desirable to use a promoter such as an alkali metal iodide. Lithium, potassium or sodium iodide may be employed. Sodium iodide is preferred. In addition, halides 6 wherein the halide is bromo are preferred.

The alkylating agents, i.e., the halides of formula 6, are commerically available or preparable by methods known in the art. For example, a 2,5,5-trialkyl-3-(4-bromobutyl)-4-thiazolidinone is preparable by the process described in U.S. Pat. No. 4,933,453 issued Jun. 12, 1990.

The heteroarenylpiperazines of the present invention are useful for treating psychoses by virtue of their ability to block apomorphine-induced climbing in mammals. Antipsychotic activity is determined in the climbing mice assay by methods similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice With: | Score |
| --- | --- |
| 4 paws on bottom (no climbing) | 0 |
| 2 paws on the wall (rearing) | 1 |
| 4 paws on the wall (full climb) | 2 |

Mice consistently climbing before the injection of apormorphine will be discarded.

With full-developed apomorphine climbing, the animals are hanging onto the cage walls, rather motionless, over long periods of time. By contrast, climbing due to mere motor stimulation usually only last a few seconds.

The climbing scores are individually totaled (maximal score: 6 per mouse over 3 readings) and the total score of the control group (vehicle intraperitoneally—apomorphone subcutaneously) is set to 100%. $ED_{50}$ values with 95% confidence limits are calculated by a Linear Regression Analysis. Antipsychotic activity expressed as the percentage decrease in climbing score of one of the instant heteroarenylpiperazines as well as a standard antipsychotic are presented in Table.

TABLE

| Compound | Dose (mg/kg of body wt.) | Antipsychotic Activity (% decrease in climbing score) |
|---|---|---|
| 1-{4-[3-[4-(thieno[2,3-b]-pyridin-3-yl)-1-piperazinyl]-propoxy]-3-methoxy-phenyl}ethanone | 14.4 | 50* |
| haloperidol (standard) | 0.33 | 50* |

*estimated dose at which a 50% decrease in the climbing score would be observed ($ED_{50}$-value)

Antipsychotic activity is achieved when the present heteroarenylpiperazines are administered to a subject requiring such treatment as an effective oral, parenteral or intravenous dose of from 0.1 to 50 mg/kg of body weight per day. A particularly preferred effective amount is about 5 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Compounds of the present invention also include:

a. 3-(4-methylpiperazinyl)thieno[2,3-b]pyridine;
b. 3-(4-benzylpiperazinyl)thieno[2,3-b]pyridine;
c. 3-[(4-methylbenzyl)piperazinyl]thieno[2,3-b]pyridine;
d. 3-[4-(3-methoxybenzyl)piperazinyl]thieno[2,3-b]pyridine;
e. 3-[4-(2-chlorobenzyl)piperazinyl]thieno[2,3-b]pyridine;
f. 3-[4-(4-trifluoromethylbenzyl)piperazinyl]thieno[2,3-b]pyridine;
g. 8-[2-(1-thieno[2,3-b]pyridin-3-yl)-4-piperazinylethyl]-8-azaspiro[4,5]decane-7,9-dione;
h. 3-{3-[1-(thieno[2,3-c]pyridin-3-yl)-4-piperazinyl]propyl}-2,5,5-trimethyl-4-thiazolidinone;
i. 3-{2-[1-(thieno[2,3-b]pyridin-3-yl)-4-piperazinyl]ethyl}-5,5-dimethyl-4-thiazolidinone S-oxide;
j. 3-[2-(1-thieno[2,3-b]pyridin-3-yl)-4-piperazinylpropyl]-2-methyl-1-thia-3-azaspiro[4,4]nonan-4-one;
k. 3-{3-[1-(thieno[2,3-c]pyridin-3-yl)-4-piperazinyl]propyl}-5,5-dimethyl-4-thiazolidinone;
l. 1-{4-[3-[4-(thieno[3,2-b]pyridin-3-yl)-1-piperazinyl]propoxy]phenyl}ethanone;
m. 1-{4-[3-[4-(thieno[3,2-b]pyridinyl-3-yl)-1-piperazinyl]propoxy]-3-methylphenyl}ethanone;
n. 1-{4-[3-[4-(thieno[2,3-b]pyridinyl-3-yl)-1-piperazinyl]propoxy]-2-bromophenyl}ethanone;
o. 1-{4-[3-[4-(thieno[3,2-c]pyridinyl-3-yl)-1-piperazinyl]propoxy]-3-trifluoromethylphenyl}ethanone;
p. N-{3-[4-[4-(thieno[2,3-b]pyridin-3-yl)-1-piperazinyl]butoxy]phenyl}acetamide;
q. N-methyl-N-{3-[4-[4-(thieno[2,3-b]pyridin-3-yl)-1-piperazinyl]butoxy]phenyl}acetamide;
r. 8-{4-[1-(thieno[3,2-c]pyridin-3-yl)-4-piperazinyl]butyl}-8-azaspiro[4,5]decane-7,9-dione;
s. 8-{4-[1-(thieno[2,3-d]pyrimidin-5-yl)-4-piperazinyl]butyl}-8-azaspiro[4,5]decane-7,9-dione;
t. 1-{4-[3-[4-(thieno[3,2-c]pyridin-3-yl)-1-piperazinyl]propoxy]-3-methoxyphenyl}ethanone;
u. 1-{4-[3-[4-(thieno[2,3-b]pyrazin-7-yl)-1-piperazinyl]propoxy]-3-methoxyphenyl}ethanone;
v. 1-{4-[3-[4-(thieno[2,3-b]pyridin-3-yl)-1-piperazinyl]propoxy]-3-hydroxyphenyl}ethanone; and
w. 1-{4-[3-[4-(thieno[2,3-b]pyridin-3-yl)-1-piperazinyl]propoxy]-3-(methylamino)phenyl}ethanone.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

All temperatures are given in °C.

EXAMPLE 1

3-(1-Piperazinyl)thieno[2,3-b]pyridine maleate

A mixture of 3-aminothieno[2,3-b]pyridine-2-carboxylic acid methyl ester (8.00 g), piperazine (6.70 g), and N-methyl-2-pyrrolidinone (80 ml) was heated to 145° C. for 3 hr, under a nitrogen atmosphere. The solution was allowed to cool, diluted with water (400 ml), and extracted with ethyl acetate. The combined extracts were washed with water and brine dried over anhydrous sodium sulfate, filtered, and the filtrate was concentrated to give 4.94 g (86.0%) of residual thieno[2,3-b]pyridine-3-amine.

The thieno[2,3-b]pyridine-3-amine (4.94 g), piperazine (16.0 g), p-toluenesulfonic acid (0.75 g), and N-methyl-2-pyrrolidinone (75 ml) was heated at reflux for 7 hr, under a nitrogen atmosphere. The reaction mixture was allowed to cool, diluted with 5% sodium hydroxide solution (400 ml) and extracted with dichloromethane. The combined extracts were washed with water, dried over anhydrous sodium sulfate, filtered, and the filtrate was concentrated under reduced pressure. The residue was chromatographed on silica gel with 30% methanol in tetrahydrofuran as the eluent. The appropriate fractions were collected and concentrated under reduced pressure. A solution of the residue (2.55 g) in ethanol was treated with maleic acid (1.35 g), partially concentrated, and cooled to room temperature to give 2.82 g (25.0%) of product, mp 163°–165°.

ANALYSIS: Calculated for $C_{13}H_{17}N_3O_4S$: 53.72% C, 5.11% H, 12.53% N. Found: 53.98% C, 5.08% H, 12.65% N.

EXAMPLE 2

3-(1-Piperazinyl)thieno[2,3-c]pyridine

A mixture of 2-carbomethoxy-3-aminothieno[2,3-c]pyridine (5.0 g), and piperazine (4.13 g) in N-methylpyrrolidinone (30 ml) was heated to 150° until decarboxyalkylation was complete. The mixture was cooled to room temperature, diluted with water, and extracted with ethyl acetate. The organic extracts were combined, dried over anhydrous magnesium sulfate, filtered, and the filtrate was concentrated in vacuo. The residual 3-aminothieno[2,3-c]pyridine, piperazine (12.5 g), p-toluenesulfonic acid (100 mg), and N-methylpyrrolidinone (50 ml) was heated under reflux (202°) overnight. The mixture was allowed to cool to room temperature, diluted with water, and extracted with dichloromethane. The organic extracts were combined, dried over anhydrous magnesium sulfate, filtered and the filtrate was concentrated in vacuo, finally at 50° (0.1 mm Hg). The residue was chromatographed on silica, using 1:1 dichloromethane:methanol eluent. The appropriate fractions were combined and concentrated. Crystallization of the residue from ethyl acetate provided 0.66 g (12%) of product, mp 126°–127.5° (dried 80° 0.1 mm Hg).

ANALYSIS: Calculated for $C_{11}H_{13}N_3S$: 60.24% C, 5.97% H, 19.16% N. Found: 59.97% C, 5.62% H, 18.86% N.

EXAMPLE 3

1-{4-[3-[4-(Thieno[2,3-b]pyridin-3-yl)-1-piperazinyl]-proxpoxy-3-methoxyphenyl}ethanone A mixture of 1-[4-(3-bromopropoxy)-3-methoxyphenyl]ethanone (5.95 g), 3-(1-piperazinyl)thieno[2,3-b]pyridine (5.00 g), potassium carbonate (9.00 g), sodium iodide (0.50 g), and acetonitrile (200 ml) was heated at 80° for 18 hr, under nitrogen. The mixture was filtered, and the filtrate concentrated under reduced pressure. The residue was taken up in dichloromethane, and the solution was washed with 10% sodium hydroxide solution, water, and dried over anhydrous sodium sulfate. The mixture was filtered, and the filtrate was concentrated under reduced pressure. The residue was chromatographed on silica gel (elution with 10% methanol in dichloromethane). The appropriate fractions were collected, combined, and concentrated. The residue was recrystallized from ethyl acetate to give 4.36 g (49.5%) of product, mp 124°–126°.

ANALYSIS: Calculated for $C_{23}H_{27}N_3O_3S$: 64.92% C, 6.40% H, 9.87% N. Found: 64.77% C, 6.52% H, 9.73% N.

EXAMPLE 4

3-{4-[1-(Thieno[2,3-b]pyridin-3-yl)-4-piperazinyl]-butyl}-2,5,5-trimethyl-4-thiazolidinone hydrochloride A mixture of 2,5,5-trimethyl-3-(4-bromobutyl)-4-thiazolidinone (4.00 g), 3-piperazinylthieno[2,3-b]pyridine (3.45 g), potassium carbonate (7.90 g), sodium iodine (350 mg), and acetonitrile (200 ml) was heated at 75° for 15 hr, under nitrogen. The mixture was filtered, the filter cake was washed with dichloromethane, and the filtrate was concentrated in vacuo. The residue was taken up in dichloromethane and the solution was washed with 5% sodium hydroxide solution, water, and dried over anhydrous sodium sulfate. The mixture was filtered, and the filtrate was concentrated in vacuo. The residue was chromatographed on silica, eluting with 5% methanol in dichloromethane. The appropriate fractions were collected, combined, and concentrated. The hydrochloride salt, prepared from ethereal hydrogen chloride, was repeatedly recrystallized from ethanol/ethyl acetate to yield 1.74 g (27.0%) of product, mp 230°–234° dec.

ANALYSIS: Calculated for $C_{21}H_{30}N_4OS_2 \cdot HCl$: 55.43% C, 6.87% H, 12.31% N. Found: 55.04% C, 6.68% H, 12.24% N.

REACTION SCHEME

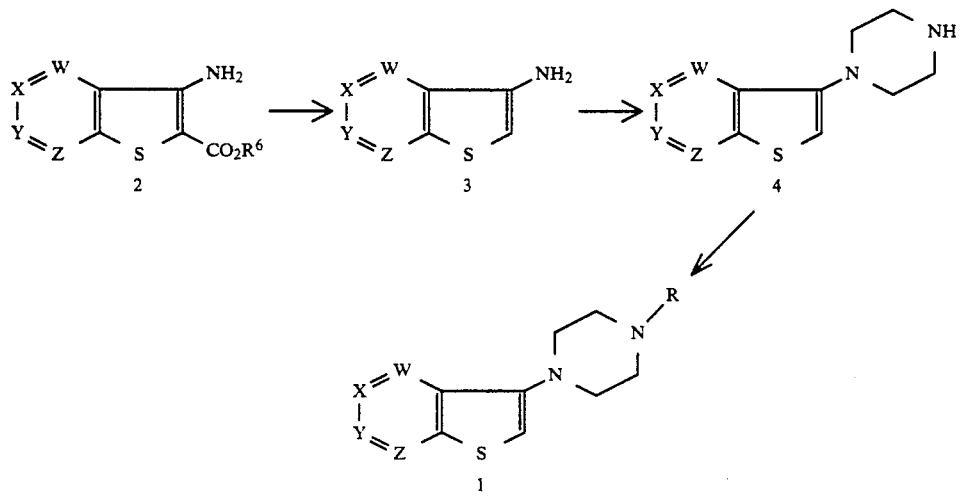

Wherein W, X, Y, Z, R and $R^6$ are as hereinbefore described

We claim:

1. A compound of the formula

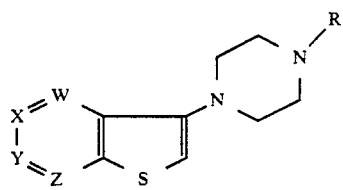

wherein:
(a) W, X, Y, and Z are independently CH or nitrogen, with the proviso that one of W, X, Y, or Z is nitrogen;
(b) R is hydrogen, loweralkyl, a group of the formula,

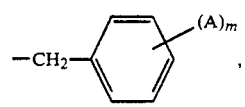

a group of the formula

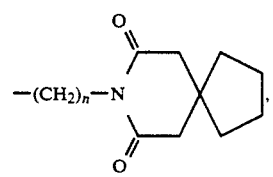

a group of the formula

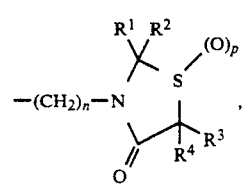

or a group of the formula

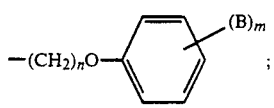

(c) $R^1$, $R^2$, $R^3$, and $R^4$ are independently hydrogen or loweralkyl; or $R^1$ and $R^2$ or $R^3$ and $R^4$ taken together with the carbon atom to which they are attached form a cycloalkyl ring;
(d) A is hydrogen, loweralkyl, loweralkoxy, halogen, or trifluoromethyl;
(e) B is hydrogen, loweralkyl, loweralkoxy, hydroxy, amino, aminoloweralkyl, halogen, trifluoromethyl, a group of the formula

loweralkyl, or a group of the formula

wherein $R^5$ is loweralkyl, loweralkoxy, amino, loweralkylamino, or diloweralkylamino;
(f) m is 1 or 2;
(g) n is 2 to 4;
(h) p is 0, 1, or 2,
the optical antipodes thereof, or the pharmaceutically acceptable acid addition salts thereof.

2. A compound according to claim 1 wherein W, X, and Y are CH and Z is nitrogen.

3. A compound according to claim 1 wherein W, X, and Z are CH and Y is nitrogen.

4. A compound according to claim 2 wherein R is hydrogen.

5. A compound according to claim 2 wherein R is a group of the formula

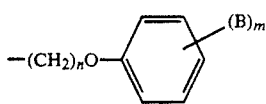

wherein B is loweralkoxy or a group of the formula

wherein R⁵ is loweralkyl.

6. A compound according to claim 2 wherein R is a group of the formula

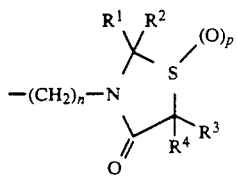

wherein R¹ is hydrogen; R², R³, and R⁴ are loweralkyl; and p is 0.

7. A compound according to claim 3 wherein R is hydrogen.

8. A compound according to claim 3 wherein R is hydrogen; A group of the formula

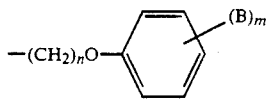

wherein B is loweralkoxy or a group of the formula

wherein R⁵ is loweralkyl.

9. A compound according to claim 3 wherein R is a group of the formula

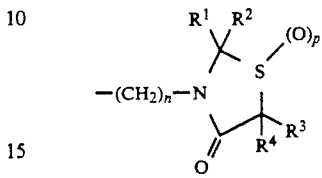

wherein R¹ is hydrogen; R², R³, and R⁴ are loweralkyl; and p is 0.

10. The compound according to claim 4 which is 3-(1-piperazinyl)thieno[2,3-b]pyridine.

11. The compound according to claim 7 which is 3-(1-piperazinyl)thieno[2,3-c]pyridine.

12. The compound according to claim 5 which is 1-{4-[3-[4-(thieno[2,3-b]pyridin-3-yl)-1-piperazinyl]-propoxy]-3-methoxyphenyl}ethanone.

13. The compound according to claim 6 which is 3-{4-[4-(thieno[2,3-b]pyridin-3-yl)-4-piperazinyl]butyl}-2,5,5-trimethyl-4-thiazolidinone.

14. A method of treating psychoses comprising administering to a mammal in need of psychoses treatment of psychoses-treating, effective amount of a compound as defined in claim 1.

15. A psychoses-treating composition comprising an adjuvant and, as the active ingredient, an amount effective in treating psychoses of a compound as defined in claim 1.

* * * * *